United States Patent [19]

Donatsch et al.

[11] Patent Number: 5,017,582
[45] Date of Patent: May 21, 1991

[54] METHOD OF INDUCING A SEROTONIN M RECEPTOR ANTAGONIST EFFECT WITH N-QUINUCLIDINYL-BENZAMIDES

[75] Inventors: Peter Donatsch, Allschwil, Switzerland; Günter Engel, Weil, Fed. Rep. of Germany; Bruno Hügi, Pfeffingen; Brian P. Richardson, Magden, both of Switzerland; Paul A. Stadler, late of Biel-Benken, Switzerland, by Hildegard R. Stadler, Brigitte M. Stadler, Sigrid A. Stadler, heirs; Gerald Breuleux, legal representative, Zürich, Switzerland

[73] Assignee: Sandoz Ltd., Basel, Switzerland

[21] Appl. No.: 466,550

[22] Filed: Jan. 17, 1990

Related U.S. Application Data

[60] Division of Ser. No. 272,030, Nov. 15, 1988, Pat. No. 4,910,207, which is a division of Ser. No. 125,048, Nov. 25, 1987, Pat. No. 4,803,199, which is a continuation of Ser. No. 896,552, Aug. 14, 1986, abandoned, which is a continuation of Ser. No. 637,952, Aug. 6, 1984, abandoned, which is a continuation of Ser. No. 508,902, Jun. 28, 1983, abandoned.

[30] Foreign Application Priority Data

| Jun. 29, 1982 | [CH] | Switzerland | 3979/82 |
| Jul. 13, 1982 | [CH] | Switzerland | 4267/82 |
| Nov. 30, 1982 | [CH] | Switzerland | 6950/82 |
| Nov. 30, 1982 | [CH] | Switzerland | 6951/82 |
| Dec. 22, 1982 | [CH] | Switzerland | 7494/82 |
| Dec. 22, 1982 | [CH] | Switzerland | 7495/82 |
| Mar. 9, 1983 | [CH] | Switzerland | 1256/83 |

[51] Int. Cl.$^5$ ............................................. A61K 31/44
[52] U.S. Cl. ............................................................ 514/305
[58] Field of Search ........................................... 514/305

[56] References Cited

U.S. PATENT DOCUMENTS

| 2,478,134 | 5/1955 | Stoll et al. | 273/127 R |
| 3,170,927 | 2/1965 | Nádor et al. | 546/129 |
| 3,342,826 | 9/1967 | Miller et al. | 546/224 |
| 3,405,134 | 10/1968 | Judd | 546/137 |
| 3,702,324 | 11/1972 | Skinner et al. | 546/133 |
| 4,093,734 | 6/1978 | Kruger et al. | 546/133 |
| 4,213,983 | 7/1980 | Hadley et al. | 546/138 |
| 4,273,778 | 6/1981 | Hadley et al. | 546/124 |
| 4,459,300 | 7/1984 | Watts | 514/214 |
| 4,499,099 | 2/1985 | Watts | 514/299 |
| 4,657,911 | 4/1987 | Imbert et al. | 546/133 |

FOREIGN PATENT DOCUMENTS

| 13138 | 12/1979 | European Pat. Off. . |
| 42705 | 12/1981 | European Pat. Off. . |
| 67770 | 12/1982 | European Pat. Off. . |
| 111607 | 12/1982 | European Pat. Off. . |
| 68700 | 1/1983 | European Pat. Off. . |
| 76592 | 4/1983 | European Pat. Off. . |
| 81054 | 6/1983 | European Pat. Off. . |
| 99789 | 2/1984 | European Pat. Off. . |
| 115933 | 8/1984 | European Pat. Off. . |
| 127529 | 12/1984 | European Pat. Off. . |
| 3322574 | 12/1983 | Fed. Rep. of Germany . |
| 2531083 | 2/1984 | France . |
| 6807287 | 11/1968 | Netherlands . |
| 774858 | 5/1957 | United Kingdom . |
| 1293446 | 10/1972 | United Kingdom . |
| 2042522 | 9/1980 | United Kingdom . |
| 2088364 | 6/1982 | United Kingdom . |
| 2125398 | 3/1984 | United Kingdom . |
| 84/03281 | 8/1984 | World Int. Prop. O. . |

OTHER PUBLICATIONS

Chem. Abstracts, 205997w, (1983).
Chem. Abstracts, 156533e, (1975).
J. of Amer. Chem. Soc., vol. 76, pp. 2855–2862, (1954).
Liebigs Ann. Chem., pp. 209–216, (1967).
Hoppe-Seyler's Z. Physiol. Chem., pp. 768–774, (1967).
J. of Het. Chem., vol. 16, pp. 625–631, (1979).
Chem. Abstracts, 14238q, (1971).
Chem. Abstracts, 123907n, (1979).
Chem. Abstracts, 22111t, (1967).
Chem. Abstracts, 209629q, (1983).
Journal of Med. Chem., vol. 21, No. 7, pp. 628–633, (1978).
Journal of Med. Chem., vol. 25, No. 2, pp. 145–152, (1982).
Pharm. Zeit, No. 40, pp. 1455 and 1456, (1972).
Derwent Abstracts, 0006591, (1963).
Acta. Chim. Acad. Scien., vol. 51, pp. 327–338, (1967).
Izv. Akad. Nauk. Arm. SSR, Biol.Nauk., vol. 15, No. 12, pp. 3–14, (1962).
Acta. Biologica Szeged., vol. 21, pp. 113–125, (1975).
Chem. Abstracts, 83522w, (1976).
Naunyn-Schmiedebergs Arch. Pharmacol. Exp. Path., vol. 259, pp. 34–44, (1967).
J. of Org. Chem., vol. 31, pp. 3482–3489, (1966).
Chem. Pharm. Bull., vol. 18, No. 10, pp. 2050–2057, (1970).
Khim.-Farm. Zh., vol. 7, No. 8, pp. 492–496, (1973).
J. of Pharm. Sciences, vol. 57, pp. 684 and 685, (1968).
Chem. Abstracts, 22632h, (1960).
Proceedings of the B.P.S., pp. 499 and 500, (Sep. 7th–9th, 1977).

*Primary Examiner*—Bernard I. Dentz
*Attorney, Agent, or Firm*—Gerald D. Sharkin; Robert S. Honor; Joseph J. Borovian

[57] ABSTRACT

The dicarboxylic, heterocyclic and substituted benzoic acid alkylene bridged piperidyl amides and esters are serotonin M antagonists.

2 Claims, No Drawings

METHOD OF INDUCING A SEROTONIN M RECEPTOR ANTAGONIST EFFECT WITH N-QUINUCLIDINYL-BENZAMIDES

This is a division of application Ser. No. 07/272,030, now U.S. Pat. No. 4,910,207, filed Nov. 15, 1988, which in turn is a division of application Ser. No. 07/125,048, filed Nov. 25, 1987, now U.S. Pat. No. 4,803,199, which in turn is a continuation of application Ser. No. 06/896,552, filed Aug. 14, 1986, now abandoned, which in turn is a continuation of application Ser. No. 06/637,952, filed Aug. 6, 1984, now abandoned, which in turn is a continuation of application Ser. No. 06/508,902, filed June 28, 1983, now abandoned.

This invention relates to benzoic acid piperidyl ester derivatives, including analogous of benzoic acid e.g. polycarbocylic and heterocyclic carboxylic acids.

The present invention provides a compound of formula I $$A-CO-B-D \qquad I$$

wherein
A is a group of formula II

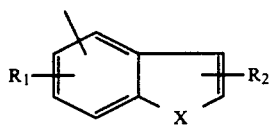

wherein
the free valence is attached to the fused benzene ring,
X is $-CH_2-$, $-NR_3-$, $-O-$, or $-S-$,
$R_1$ and $R_2$ independently are hydrogen, halogen, $(C_{1-4})$alkyl $(C_{1-4})$alkoxy, hydroxy, amino, $(C_{1-4})$alkylamino, di$(C_{1-4})$alkylamino, mercapto, or $(C_{1-4})$alkylthio, and
$R_3$ is hydrogen, $(C_{1-4})$alkyl, $(C_{3-5})$alkenyl, aryl, or aralkyl,
or a group of formula III

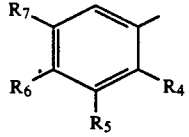

wherein $R_4$ to $R_7$ independently are hydrogen, amino, nitro, $(C_{1-4})$alkylamino, di$(C_{1-4})$alkylamino, halogen, $(C_{1-4})$alkoxy, $(C_{1-4})$alkyl,$(C_{1-4})$alkanoylamino or pyrrolyl, with the proviso that at least one of $R_4$ and $R_5$ is other than hydrogen,
B is $-O-$ or $-NH-$,
D is a group of formula IV

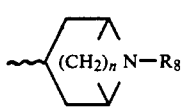

wherein
n is 2, 3 or 4,
$R_8$ is hydrogen, $(C_{1-7})$alkyl, $(C_{3-5})$alkenyl, or aralkyl,
or a group of formula V

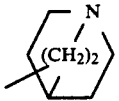

with the further provisos (i) that when A is a group of formula III, and B is $-NH-$, then D is a group of formula V, (ii) that when A is a group of formula III wherein either $R_4$ is hydrogen, or wherein $R_4$ is halogen or alkyl and $R_5$ to $R_7$ are chosen from halogen or hydrogen, and B is $-O-$ and D is a group of formula IV, then n is 3 or 4, (iii) that when A is a group of formula III and one of $R_4$ to $R_7$ is alkoxy, and D is a group of formula V, then either one of the others of $R_4$ to $R_7$ is other than hydrogen and alkoxy or only two of $R_{4\,l\,to\,R7}$ are alkoxy, (iv) that when A is a group of formula III wherein $R_4$ is alkyl or halogen, then B is $-O-$, as well as acid addition salts and quaternary ammonium salts thereof. All these compounds are referred to as compounds of the invention.

Any alkyl moiety preferably is methyl, ethyl or propyl. Alkoxy is preferably methoxy or ethoxy. Aralkyl is conveniently aryl$(C_{1-4})$alkyl. Alkenyl is preferably allyl or methallyl. Any aryl moiety is preferably unsubstituted phenyl or phenyl mono- or poly-substituted by $(C_{1-4})$alkyl, e.g. methyl, halogen, e.g. fluorine, hydroxy, or $(C_{1-4})$alkoxy, e.g. methoxy. Preferably any substituted aryl group is mono-substituted. Aralkyl is conveniently benzyl. Halogen is fluorine, chlorine, bromine or iodine.

A is conveniently a group of formula II.

In the group of formula II, the carbonyl side chain may be attached to the ring carbon atom in positions 4,5,6 or 7 of the nucleus, but preferably in position 4 and 5. Preferably A is indole.

$R_1$ is attached to the ring carbon atom in position 4, 5, 6 or 7 of the nucleus, preferably position 5 and $R_2$ is attached to the ring carbon atom in position 2 or 3 of the nucleus. Tautomers are also covered by formula I e.g. when $R_2$ is hydroxy or mercapto in the 2 position.

$R_3$ is conveniently hydrogen or alkyl. Conveniently n is 3 or 4, more preferably 3.

In a group of formula III conveniently
$R_4$ is halogen, $(C_{1-4})$alkylamino or $(C_{1-4})$alkoxy;
$R_5$ is hydrogen or halogen;
$R_6$ is hydrogen, amino, nitro, $(C_{1-4})$alkylamino, di$(C_{1-4})$alkylamino, halogen or 1-pyrrolyl; and
$R_7$ is hydrogen or halogen.

Conveniently $R_6$ is other than hydrogen, halogen, or pyrrolyl.

In the group of formula III $R_7$ is preferably halogen and is preferably chlorine or iodine and especially chlorine.

Other examples of the group of formula III include 3,5-dimethoxyphenyl, 3,5-dimethylphenyl and especially 3,5-dichlorophenyl. Alternatively the group of formula III may be 3-chloro, 3-methyl or 3,4,5-trimethoxyphenyl.

The group IV may exist in different conformations. For example the six-membered ring containing the nitrogen atom and the carbon atom to which the B-moiety is attached-hereafter referred to as the piperidyl ring may exist in the chair or boat conformations or in an intermediate conformation.

The moiety B may have two different configurations. These can be appreciated by making group IV have a conformation wherein a reference plane may be drawn through the carbon atoms of the piperidyl ring and the nitrogen atom is above the plane and the alkylene bridge is below the plane. The B moiety has the α conformation when it is below the plane on the same side as the alkylene bridge. This corresponds to the endo configuration and also to the configuration in tropine etc. The B moiety has the β-configuration when it is above the plane on the same side as the nitrogen bridge. This corresponds to the exo configuration and also the configuration in pseudotropine etc. Used hereinafter is the exo/endo nomenclature. The endo isomers are preferred.

$R_8$ is preferably alkyl and especially methyl.

A group of formula V is also known as quinuclidinyl. Conveniently this is 3- or 4-quinuclidinyl and especially 3-quinuclidinyl.

A group of compounds comprises compounds of formula Ipa

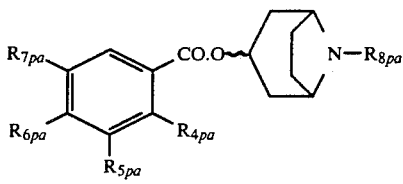

wherein
$R_{4pa}$ is halogen, $(C_{1-4})$alkylamino, or $(C_{1-4})$alkoxy,
$R_{5pa}$ is hydrogen,
$R_{6pa}$ is amino, $(C_{1-4})$alkylamino, or di$(C_{1-4})$alkylamino,
$R_{7pa}$ is hydrogen or fluorine, chlorine or bromine, and
$R_{8pa}$ is hydrogen, $(C_{1O7})$alkyl or aralkyl,
as well as acid addition salts and quaternary ammonium salts thereof.

Another group of compounds comprises benzoic acid isopelletierine (homotropane) esters, in particular compounds of formula Ipb

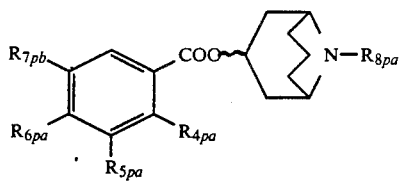

wherein
$R_{4pa}$, $R_{5pa}$, $R_{6pa}$, $R_{8pa}$ are as defined above and
$R_{7bp}$ is hydrogen or halogen,
as well as acid addition salts and quaternary ammonium salts thereof.

A group of compounds comprises compounds of formula Iqa

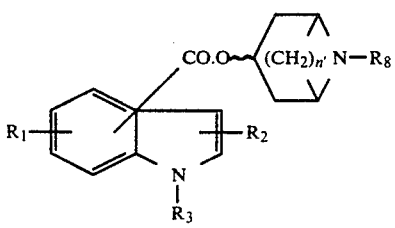

wherein the free valence is attached to the fused benzene ring, and
n' is 2 or 3, and
$R_1$, $R_2$, $R_3$ and $R_8$ are as defined above,
as well as acid addition salts and quaternary ammonium salts thereof.

Another group of compounds comprises indole carboxylic acid tropine and isopelletierine (homotropane) esters, particularly of formula Iqb

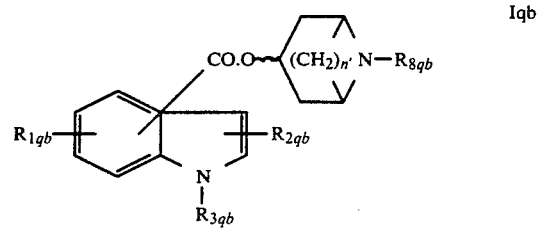

wherein
the free valence is attached to the fused benzene ring, and $R_{1qb}$ and $R_{2qb}$ are independently hydrogen, halogen or $(C_{1-4})$alkyl,
$R_{3qb}$ is hydrogen or $(C_{1-4})$alkyl,
$R_{8qb}$ is hydrogen or $(C_{1-7})$alkyl or aralkyl, and
n' is as defined above,
as well as acid addition salts and quaternary ammonium salts thereof.

A further group of compounds comprises indole carboxylic acid tropine and isopelletierine (homotropane) amides, in particular of formula Iqc

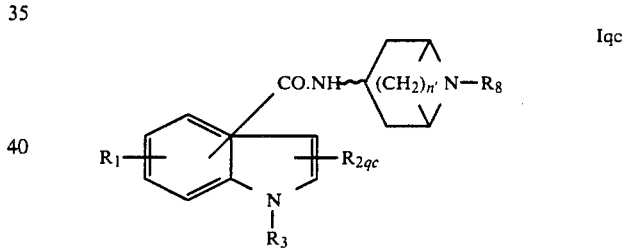

wherein
the free valence is attached to the fused benzene ring,
$R_{2qc}$ is as $R_2$ defined above other than $(C_{1-4})$alkoxy and hydroxy and,
n', $R_1$, $R_3$, $R_8$ are as defined above,
as well as acid addition salts and quaternary ammonium salts thereof.

Another group of compounds comprises benzoic acid quinuclidinyl esters, in particular compounds of formula Isa

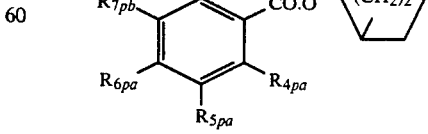

wherein $R_{4pa}$, $R_{5pa}$, $R_{6pa}$ and $R_{7pb}$ are as defined above as well as acid addition salts and quaternary ammonium salts thereof.

A further group of compounds comprises benzoic acid quinuclidinyl amides in particular compounds of formula Isb

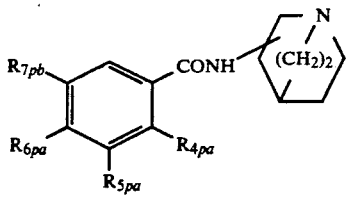

wherein R4pa, R5pa, R6pa and R7pb are as defined above, as well as acid addition salts and quaternary ammonium salts thereof.

The present invention furthermore provides a process for the production of a compound of the invention which includes the step of condensing an appropriate di-carbocyclic or heterocyclic carboxylic acid or benzoic acid or a reactive acid derivative thereof, or a precursor of the acid or derivative, with an appropriate alkylene bridged piperidyl amine or piperidinol, or a precursor thereof, and as necessary converting the resultant piperidyl ester or amide, or acid addition salt or quaternary ammonium salt thereof into the required piperidyl ester or amide or acid addition salt or quaternary ammonium salt thereof and recovering the resultant piperidyl ester or amide as such or as an acid solution salt or as a quaternary ammonium salt thereof.

In particular the present invention provides a process for the production of a compound of formula I as well as acid addition salts thereof or quaternary ammonium salts thereof which includes the step of a) condensing an appropriate compound of formula VI

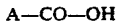

A—CO—OH                VI wherein A is as defined above, a reactive derivative thereof, or a precursor of the acid or derivative, with an appropriate compound of formula VII

HB—D                VII wherein B and D are as defined above, or a precursor of the compound, or b) alkylating a compound of formula I having a secondary amino group to produce a compound of formula I with a tertiary amino group, c) deprotecting any protected form of a compound of formula I to obtain a compound of formula I, d) halogenating a compound of formula I wherein A is a group of formula II and $R_2$ is hydrogen to obtain the corresponding compound wherein $R_2$ is halogen, or e) alkoxylating a compound of formula I wherein A is a group of formula II and $R_2$ is halogen to obtain the corresponding compound wherein $R_2$ is alkoxy, and recovering the resultant compound of formula I as such or as an acid addition salt or as a quaternary ammonium salt thereof.

The condensation process of the invention to obtain amides and esters may be effected in conventional manner for analogous compounds.

For example the carboxylic acid group may be activated in the form of a reactive acid derivative, especially for the production of amides.

Suitable reactive acid derivatives may be formed by reaction with N,N'-carbonyl-diimidazole producing an intermediate carboxylic acid imidazolide, or with N-hydroxy-succinimide. Alternatively an acid chloride may be used, e.g. produced by reaction with oxalyl chloride.

For production of esters, the alcohol may be used e.g. in the form of an alkali metal salt, preferably the lithium salt. Such salts may be produced in conventional manner, e.g. by reaction of a n-butyl lithium with the alcohol in tetrahydrofuran. If desired a heterocyclic or tertiary amine, e.g. pyridine or triethylamine, may be present, especially for the production of amides.

Suitable reaction temperatures may be from about $-10°$ to about $10°$. In the case of compounds wherein B is NH and D is a group of formula V the reaction temperature may be for example up to about 100° C., e.g. in boiling methanol or ethanol.

Other suitable inert organic solvents include, e.g. tetrahydrofuran or dimethoxyethane.

In these reactions the endo or exo configuration of the substituent B in the group of formula IV is believed to be maintained. The compound of formula VII may be reacted if desired as a mixture of endo and exo isomers and the pure endo or exo isomer isolated, e.g. by chromatography or crystallization.

The compounds of the invention may be converted into other compounds of the invention, e.g. in conventional manner. Some interconversions are exemplified in process b), c), d) and e).

The alkylation reaction of process b) may be effected in conventional manner. Any free amino group may be alkylated, especially compounds of formula II wherein $X=NH$. Appropriate alkylation conditions include reaction with an alkyl halide in the presence of a sodium alcoholate. Suitable temperatures may be from about $-50°$ to about $-30°$ C.

The deprotection reaction of process c) is specifically suitable for the production of compounds with secondary amino groups, e.g. $R_8=H$ in the group of formula IV or primary amino groups, e.g. $R_6=NH_2$.

For example a compound of formula I may be produced in protected form, e.g. $R_8$ being replaced by a secondary amino protecting group such as benzyl. The benzyl group may be split off in conventional manner, e.g. by hydrogenation to produce the corresponding compound of formula I wherein $R_8$ is hydrogen. Suitable the hydrogenation may be effected in the presence of a palladium on active charcoal at room temperature or at a slightly elevated temperature. Suitable solvents include acetic acid, ethyl acetate or ethanol.

A primary amino group as $R_6$ may be protected by e.g. N-benzyloxycarbonyl. This group may be split off by hydrogenation analogously to that indicated above. In the presence of a benzyl group the N-benzyloxycarbonyl group is generally split off first so that this group may be selectively split off.

Also the amino group may be in the form of a nitro group. This can be selectively reduced in conventional manner, e.g. by iron in hydrochloric acid.

Halogenation according to process d) may be effected in conventional manner. For example with N-chloro-succinimide may lead to chlorination. Such reactions may be effected in a suspension in chloroform. Reaction with N-iodo-succinimide may alternatively lead to iodination.

Replacement of reactive halogen groups according to process e) may be effected in conventional manner e.g.

by reaction with an appropriate alcohol at e.g. room temperature from 10 to 20 hours at least.

A precursor of a starting material may be employed if desired. Such a precursor may be capable of being converted into the starting material is conventional manner but instead the process of the invention is carried out with the precursor and the other starting material or materials or a precursor thereof. The resultant product is converted into the compound of the invention in conventional manner, e.g. by using the same reaction conditions by which the precursor may be converted into the starting material. Typical precursors include protected forms of a starting material, e.g. wherein amino groups are temporarily protected.

The compounds of the invention may be isolated and purified in conventional manner.

Insofar as the production of any starting material is not particularly described herein, it is known, or may be produced in analogous manner to known compounds, in analogous manner to that described herein, e.g. the examples, or to known procedures for analogous compounds.

Compounds of formula VII wherein B is —NH—, D is a group of formula IV wherein n is 4 are new. These compounds have never been specifically suggested before although they fall under various generic disclosures.

The compounds are useful intermediates e.g. for the preparation of amides as described herein which have an interesting pharamcological profile and e.g. have never been disclosed as Serotonin M antagonists and having other activities disclosed hereinafter. These compounds of formula VII may for example be produced by reduction of the corresponding oxime, like the other compounds of formula VII wherein B is —NH—. Compounds of formula VII wherein B is —O— may be produced in conventional manner by reduction of the corresponding ketone.

All the above reductions may be effected, e.g. by catalytic hydrogenation, e.g. over platinum (believed to lead primarily to endo isomers), Bouveault-Blanc reaction procedures, e.g. sodium/amyl alcohol or butanol (believed to lead primarily to exo isomers), or aluminium hydride procedures, or sodium borohydride (often leading to a mixture of endo/exo isomers).

Any mixture of the exo and endo forms may be separated by chromatography.

Free base forms of compounds of the invention may be converted into salt forms. For example acid addition salts may be produced in conventional manner by reacting with a suitable acid, and vice versa. Suitable acids for salt formation include hydrochloric acid, malonic acid, hydrobromic acid, maleic acid, malic acid, fumaric acid, methanesulphonic acid, oxalic acid, and tartaric acid. Quaternary ammonium salts of the compounds of the invention may be produced in conventional manner, e.g. by reaction with methyl iodide.

In the following examples all temperatures are in degrees Centigrade and are uncorrected. All n.m.r. spectra values are in ppm (tetramethylsilane=0 ppm).

Nomenclature

Endo-8-methyl-8-aza-bicyclo[3.2.1]oct-3-yl=tropyl or α-tropyl

Exo-8-methyl-8-aza-bicyclo[3.2.1]oct-3-yl=pseudo- or β-tropyl

Endo-9-methyl-9-aza-bicyclo[3.3.1]non-3-yl=isopelletierinyl or α-homo-tropanyl

Exo-9-methyl-9-aza-bicyclo[3.3.1]non-3-yl=β-isopelletierinyl or β-homotropanyl or pseudopelletierinyl 1-aza-bicyclo[2.2.2]octyl=quinuclidinyl In the tables the column heading "configuration" gives the indicated configuration of the group B-D, i.e. endo or exo. The column heading "Prep" gives the number of the Example in the A series describing the preparation process.

Abbreviations used:
III-I = 5-chloro-2-methoxy-4-methylaminophenyl
III-II = 2-methoxy-4-dimethylaminophenyl
III-III = 4-amino-5-chloro-2-methoxyphenyl
III-IV = 4-amino-2-methoxyphenyl
III-V = 3-iodo-2-methoxy-4-methylaminophenyl
III-VI = 5-chloro-2-methoxy-4-dimethylaminophenyl
III-VII = 2-chloro-4-aminophenyl
III-VIII = 3-iodo-4-amino-2-methoxyphenyl
III-IX = 2-methoxy-4-methylamino-phenyl
III-X = 2-chloro-4-nitrophenyl
III-XI = 4-bromo-2-methoxyphenyl
III-XII = 3,5-dichlorophenyl
III-XIII = 5-chloro-2-methoxy-4-(1-pyrrolyl)phenyl
III-XIV = 2-methoxy-4-(1-pyrrolyl)phenyl 1) hydrogen maleate
2) hydrogen malonate
3) decomposition
4) bis [base] fumarate
5) obtained by reduction of corresponding 4-nitro compound
6) hydrobromide
7) via imidazolyl intermediate
8) exo form has C-3 H broad multiplet at ca 5.15 ppm in H¹N.M.R. endo form has C-3 H double triplet at 5.1 ppm. Exo alcohol is eluted before endo isomer on silica gel-eluant $CH_2Cl_2$/5% $CH_3OH$/5% $NH_4OH$
9) hydrogen oxalate
10) in presence of triethylamine instead of pyridine

EXAMPLE 1

Preparation of starting materials a) Indol-4-yl carboxylic acid chloride 32.2 g (0.2 M) dry indol-4-yl carboxylic acid are suspended in 150 ml absolute methylene chloride, 26 ml (0.3 M) oxalyl chloride are added to the stirred mixture at 20° over 30 minutes. Gas evolution results. The mixture is stirred for 3½ hours at 20° C. 150 ml Hexane are added. The mixture is stirred for another 20 minutes and the resultant heading compound filtered off, washed with methylene chloride/hexane 1:1 dried at 20° in a vacuum to give beige crystals, which are used further without purification.

b) 9-methyl-9-aza-bicyclo[3.3.2]nonan-3-one oxime (also called 3-homotropanone oxime)

176 g (2.15 N) sodium acetate and 150 g (2.15 M) hydroxylamine hydrochloride are pounded in a mortar to a thin paste, extracted with 1 liter methanol, the salt filtered off and the solution treated with 99.5 g (0.65 M) endo-9-methyl-9-aza-bicyclo[3.3.1]nonan-3-one (3-homotropane). The oxime beings to crystallize after 10 minutes and the mixture is stirred for another 4 hours at 20° C. To work up the mixture is concentrated under a vacuum, the residue treated with potassium hydrogen carbonate solution and extracted with chloroform containing some isopropanol. The combined organic phases are washed with a little water, dried with sodium sulphate and concentrated to give the heading compound, M.pt. 126°–127° (from toluene/hexane).

c) Endo-9-methyl-9-aza-bicyclo[3.3.1]non-3-yl amine (also called 3α-amino-homotropane)

A solution of 50.5 ml (0.95 M) concentrated sulphuric acid in 200 ml absolute terahydrofuran are added to a cooled and stirred mixture of 73 g (1.9 M) lithium aluminium hydride in 900 ml absolute tetrahydrofuran at $-10°$ C. within 2 hours. The mixture is allowed to stand overnight. A solution of 80 g (0.475 M) endo-9-methyl-9-aza-bicyclo[3.3.1]nonan-3-one oxime in 1.4 liters absolute tetrahydrofuran is added dropwise over 30 minutes to the stirred mixture at 30° and allowed to react further at 40° for 3 hours. To work up the reaction mixture is cooled to 10° and a mixture of 150 ml water in 150 ml tetrahydrofuran is added carefully. The mixture is stirred for an hour at 30° C. The resultant precipitate is filtered off. The residue is washed with methylene chloride and ether The organic phases are combined and distilled to give the heading compound b.pt. 115°–119° (17–18 Torr)—$n_D^{20} = 1.5066$.

(As will be appreciated the reduction gives mainly the endo product. Analogous reaction of 8-methyl-8-aza-bicyclo[3.2.1]octan-3-one oxime gives the exo product).

EXAMPLE A-2

Indol-4-yl carboxylic acid endo-8-methyl-8-aza-bicyclo[3.2.1]oct-3-yl ester (process a)

(Compound of formula I wherein $A=II$ in 4 position; $R_1=R_2=H$; $X=NH$; $B=O$; $D=IV$ in α configuration; $n=2$; $R_8=CH_3$)

6.35 g (45 mM) endo-8-methyl-8-aza-bicyclo[3.2.1]octan-3-ol (Tropine) in 20 ml absolute tetrahydrofuran are treated at 0° to 10° with 17 ml of a 2 molar solution of butyl lithium in hexane. The mixture is stirred for a further 30 minutes. The hexane is removed under a vacuum and replaced by a corresponding amount of tetrahydrofuran to give the lithium salt.

4.8 g (27 mM) of indol-4-yl carboxylic acid chloride in 20 ml tetrahydrofuran are added to the mixture and the beige suspension stirred overnight at 20° C. The mixture is worked up in the usual manner partitioning between methylene chloride and sodium carbonate to give the heading compound in crude form which is chromatographed on silicagel (250 g) eluting the heading compound with methylene chloride containing 10% methanol and 0.5% ammonia.

Alternatively indol-4-yl carboxylic acid chloride may be reacted with N,N'-carbonyl di-imidazole to form the imidazolide. This may be reacted with the above lithium salt at 10° to 15° in tetrahydrofuran.

EXAMPLE A-3

Alkylation of indole amide 0.46 g (20 mM) sodium dissolved in 170 ml dry liquid ammonia at $-50°$ are treated dropwise with 1.3 ml (22.5 mM) absolute ethanol diluted with some absolute ether. The resultant colourless suspension of sodium ethanolate is stirred for 15 minutes at $-50°$. 4.46 g indol-yl carboxylic acid amide are added giving a clear solution. The mixture is stirred for 10 minutes at $-50°$ and 1.25 ml (20 mm) methyl iodide in 4 ml absolute ether is added.

The mixture is stirred at $-50°$ for a further 4½ hours. To work up the ammonia is removed in a vacuum. The residue is partitioned between methylene chloride and water and worked up in the usual manner to give a colourless foam which is chromatographed in 120 g silicagel eluting with methylene chloride containing 5% methanol/3% ammonia to obtain the 1-methyl compound from the acid.

a) Indolyl carboxylic acid amides as starting materials may be produced by reacting an indolyl carboxylic acid chloride in absolute methylene chloride with an amine in the presence of pyridine at $-10°$ to 0°.

EXAMPLE A-4

Debenzylation 4.9 g of N-benzyl indol-yl carboxylic acid ester in 200 ml ethanol are hydrogenated at room temperature and normal pressure in the presence of 1.5 g (10%) palladium on active charcoal catalyst. After 45 minutes the uptake of ca 230 ml hydrogen is finished and the catalyst filtered off. The solvent is removed in a vacuum to give a crystalline residue of the nor compound.

EXAMPLE A-5

Chlorination and alkoxylation 5.68 g indol-yl carboxylic acid aza ester is added to a stirred suspension of 4 g (30 mM) N-chlorosuccinimide in 80 ml absolute chloroform at 20° C. The mixture is stirred for 3 hours at 20° to give 2-chloro-indol-yl carboxylic acid ester in a clear yellow solution.

The clear yellow solution is treated with 10 ml absolute methanol and allowed to stand overnight. Usual working up by partitioning the mixture between 1N aqueous sodium carbonate and methylene chloride gave a crude product which is chromatographed on silicagel (30 fold amount) eluting with methylene chloride containing 10% methanol and 0.5% ammonia to obtain the 2-alkoxy indole.

EXAMPLE A-6

3-indo-indol-4-yl carboxylic acid endo-8-methyl-8-aza-bicyclo[3.2.1]oct-3-yl ester (compound of formula I wherein $A=II$ in 4 position, $R_1=H$; $R_2=3-I$; $X=NH$; $B=-O-$; $D=IV$ in α configuration; $n=2$; $R_8=CH_3$) (process d)

A solution of 2.84 g (10 mM) indol-4-yl carboxylic acid endo-8-methyl-8-aza-bicyclo[3.2.1]oct-3-yl ester is added dropwise at 15° to a stirred suspension of 2.48 g (11 mM) N-iodo-succinimide in 200 ml absolute chloroform. The mixture is stirred for a further 30 minutes at 20°. Partitioning between 1N sodium carbonate solution and methylene chloride and usual working up give the heading compound 163°–165° (decomp) (from ethanol). Although the compound may be produced from 3-indo-indol-4-yl carboxylic acid in analogous manner to that disclosed in Example 2.

EXAMPLE A-7

5-chloro-2-methoxy-4-methylamino-benzoic acid 1-aza-bicyclo[2.2.2]oct-3-yl ester also called 5-chloro-2-methoxy-4-methylamino-benzoic acid quinuclidin-3-yl ester (process a)

(Compound of formula I wherein A=III; $R_4$=OCH$_3$; $R_5$=H; $R_6$=NHCH$_3$; $R_7$=Cl; B=—O—; D=V in 3 position)

a) 5-chloro-4-methylamino-2-methoxy-benzoic acid imidazolide 12 g N,N'-carbonyl-diimidazole are added to a stirred solution of 8 g 5-chloro-4-methylamino-2-methoxy-benzoic acid in 300 ml dry tetrahydrofuran at 20° to 25°. The mixture is stirred under anhydrous conditions for 1 hour, and the solvent removed at 35° to 40°. The residue is dissolved in methylene chloride.

The mixture is washed 2 to 3 times with water, dried over magnesium sulphate, filtered and concentrated. The heading compound crystallises from methylene chloride/hexane. M.pt. 152°–154°.

b) 5-chloro-4-methylamino-2-methoxy-benzoic acid 1-aza-bicyclo[2.2.2]oct-3-yl ester 27 ml n-butyl lithium (1.6 Molar) in hexane is added dropwise to a stirred solution of 5.56 g 1-aza-bicyclo[2.2.2]octan-3-ol (quinuclidin-3-ol) in 100 ml absolute tetrahydrofuran at 0° to 5° under dry nitrogen. The mixture is stirred for a further 10 to 15 minutes at 0° to 5° and then a solution of 5-chloro-4-methylamino-2-methoxy-benzoic acid imidazolide in 100 ml absolute tetrahydrofuran is added. It is stirred for an hour. 5 ml saturated aqueous potassium hydrogen carbonate solution is added and the solution is decanted. The residue is washed twice with terahydrofuran. The combined organic phases are dried over magnesium sulphate, filtered and concentrated. The crude product is treated with an equivalent amount of malonic acid to give the heading compound in hydrogen malonate form. M.pt. 170°–172° (from acetone).

EXAMPLE A-8

4-amino-5-chloro-2-methoxy-benzoic acid exo-8-benzyl-8-aza-bicyclo[3.2.1]oct-3-yl ester also called 4-amino-5-chloro-2-methoxy-benzoic acid 8-benzyl pseudo-nor-tropyl ester (process c)

(Compound of formula I wherein A=III; $R_4$=OCH$_3$; $R_5$=H; $R_6$=NH$_2$; $R_7$=Cl; B=O; D=IV in $\beta$ configuration; n=2; $R_8$=benzyl)

a) 4-(N-benzyloxycarbonyl)amino-2-methoxy-benzoic acid methyl ester

A solution of 42.1 g 4-amino-2-methoxy-benzoic acid methyl ester in 600 ml toluene is boiled under reflux for 2½ hours together with 60 ml chloroformic phenyle ester. The solution is cooled and crystals of the heading compound filtered off. M.pt. 137°–138°.

b) 4-(N-benzyloxycarbonylamino)-5-chloro-2-methoxy-benzoic acid methyl ester 18 g chlorine gas (dried over sulphuric acid) is passed through a stirred solution of 61.4 g 4-(N-benzyloxycarbonyl)amino-2-methoxy-benzoic acid methyl ester in 1 liter chloroform at 20° for 20 to 25 minutes. The reaction mixture is concentrated under a vacuum to give the crystals of the heading compound which is reacted further as such.

c) 4-(N-benzyloxycarbonylamino)-5-chloro-2-methoxy-benzoic acid 200 ml 2N aqueous sodium hydroxide solution is added dropwise to a stirred solution of 72.1 g of the benzoic acid methyl ester produced in step b) in 800 ml dioxane. The mixture is stirred for 20 hours and the organic solvent removed under a vacuum. The residue is dissolved in water and adjusted to pH 5–6 with 3N hydrochloric acid. The heading compound is filtered off and washed with water. M.pt. 182°–183° (from methanol).

d) 4-(N-benzyloxycarbonylamino)-5-chloro-2-methoxy-benzoic acid imidazolide

The compound is produced in analogous manner to Example A-7a.

e) 4-(N-benzyloxycarbonylamino)-5-chloro-2-methoxy-benzoic acid exo-8-benzyl-8-aza-bicyclo[3.2.1]oct-3-yl ester The compound is produced in analogous manner to Example A-7b.

f) 4-amino-5-chloro-2-methoxy-benzoic acid exo-8-benzyl-8-aza-bicyclo[3.2.1]oct-3-yl ester 5.4 g 4-(N-benzyloxycarbonylamino)-5-chloro-2-methoxy-benzoic acid exo-8-benzyl-8-aza-bicyclo[3.2.1 oct-3-yl ester in 100 ml ethanol are hydrogenated in the presence of 0.7 g palladium (10%) on charcoal for 50 minutes at atmospheric pressure taking up one equivalent of hydrogen. The mixture is filtered through a filtering aid (Hyflo Supercell) and the filtrate concentrated. The residue is chromatographed on silicagel with methylene chloride containing 5% methanol and the heading compound obtained in free base form. M.pt. 241°–242° (hydrobromide produced from HBr, in ethanol).

EXAMPLE A-9

4-amino-5-chloro-2-methoxy-benzoic acid exo-8-aza-bicyclo[3.2.1]oct-3-yl ester also called 4-amino-5-chloro-2-methoxy-benzoic-acid pseudo nor-tropyl ester (process c)

(Compound of formula I wherein A=III; $R_4$=OCH$_3$; $R_5$=H; $R_6$=NH$_2$; $R_7$=Cl; B=O; D=IV in $\beta$ configuration; n=2; $R_8$=H)

8.4 g 4-(N-benzyloxycarbonylamino)-5-chloro-2-methoxy-benzoic acid exo-8-benzyl-8-aza-bicyclo[3.2.-1]oct-3-yl ester in 250 ml ethyl acetate or acetic acid are hydrogenated in the presence of 1.2 g 10% palladium on charcoal at atmospheric pressure and at 20° to 25° for 2 hours. The mixture is filtered (e.g. through Hyflo), the filtrate is evaporated and the residue dissolved in methylene chloride.

The organic phase is washed with 1N sodium hydroxide and then with water, dried over magnesium sulphate and concentrated. The product is chromatographed through silicagel using methylene chloride +5% methanol and methylene chloride +20% methanol. The title compound is crystallised as the hydrochloride. M.pt. 258°–259° (from ethanol).

EXAMPLE A-10

Indol-4-yl carboxylic acid
endo-8-methyl-8-aza-bicyclo[3.2.1]oct-3-yl ester also
called Indol-4-yl carboxylic acid tropyl ester (Compound of formula I A=II in 4 position;
$R_1=R_2=H$; $R_3=NH$; B=O; D=IV in α
configuration; n=2; $R_8=CH_3$)

7 g (50 mM) endo-8-methyl-8-aza-bicyclo[3.2.1] octan-3-ol (tropine) in 15 ml absolute tetrahydrofuran is treated at 10° to 15° dropwise with 20 ml (40 mM) of 2 Molar butyl lithium in hexane. The mixture is stirred for 30 minutes at 20°, and then concentrated to a volume of about 10 ml to remove the hexane to give the lithium enolate. 10 ml tetrahydrofuran is added.

4.8 g (30 mM) dry indol-4-yl carboxylic acid in 15 ml absolute tetrahydrofuran is treated portionwise with 5.85 g (36 mM) N,N'-carbonyl-diimidazole. The mixture is allowed to stand for 90 minutes at 20° and then is added dropwise to the lithium enolate. The resultant suspension is stirred overnight at 20° C., and partitioned between methylene chloride/a little isopropanol and 1N sodium carbonate. The organic phases are washed and dried over sodium sulphate to give an evaporation the heading compound. M.pt. 220°-222° (decomp) (from ethanol).

EXAMPLE A-11

Indol-4-yl carboxylic acid
endo-9-methyl-9-aza-bicyclo[3.3.1]non-3-yl ester also
called 3α-homotropanyl indol-4-yl carboxylic ester (Compound of formula I A=II in 4 position; X=NH;
$R_1=R_2=H$; $R_3=NH$; B=O; D=IV in α
configuration; n=3; $R_8=CH_3$) (process a)

a) 7.65 g (50 mM) endo-9-methyl-9-aza-bicyclo[3.3.1]non-3-ol in 15 ml absolute tetrahydrofuran are treated dropwise wt 10° to 15° with 20 ml (40 mM) 2 Molar butyl lithium hexane solution. The resultant mixture is stirred for 30 minutes at 20°. The hexane is then evaporated and replaced by tetrahydrofuran to give a solution of the lithium salt.

b) 4.8 g (30 mM) dry indol-4-yl carboxylic acid in 15 ml absolute tetrahydrofuran is treated portionwise at room temperature with 5.85 g (36 mM) N,N'-carbonyl-diimidazole. After gas evolution finishes the solution is allowed to stand for 90 minutes at 20° and then treated dropwise with the above lithium salt at 10° to 15°. The resultant suspension is stirred for 15 hours at 20° and partitioned between methylene chloride/little isopropanol and 1N sodium carbonate solution. The organic phase is washed with water, dried with sodium sulphate and evaporated to give the heading compound. M.pt. 189°-190° (from ethanol).

B SERIES EXAMPLES

The following compounds of formula I wherein D is a group of formula IV are produced:

| Example | A | B | n | $R_8$ | Conf. | M. pt. | Prep |
|---|---|---|---|---|---|---|---|
| 1 | indol-5-yl | O | 2 | $CH_3$ | endo | 191–193° | 2 |
| 2 | indol-5-yl | O | 3 | $CH_3$ | endo | 148–149° | 10 |
| 3 | 3-iodo-indol-5-yl | O | 3 | $CH_3$ | endo | 172–174° | 6 |
| 4 | indol-4-yl | NH | 2 | $CH_3$ | exo | 267–269°[3] | 3a |
| 5 | indol-4-yl | NH | 2 | $CH_3$ | endo | 221–223°[3] | 3a |
| 6 | indol-5-yl | NH | 2 | $CH_3$ | endo | 220–221° | 3a |

C SERIES EXAMPLES

In analogous manner to that described above the following compounds wherein A is a group of formula III and D is a group of formula IV are produced:

| Example | A | B | n | $R_8$ | Conf. | M. pt. | Prep |
|---|---|---|---|---|---|---|---|
| 1 | III-I | O | 2 | $CH_3$ | endo | 193–195°[1] | 7 |
| 2 | III-II | O | 2 | benzyl | exo | 112–114°[2] | 7 |
| 3 | III-III | O | 2 | $CH_3$ | endo | 154–155°[2] | 7 |
| 4 | III-III | O | 2 | H | endo | 168–169°[2] | 9 |
| 5 | III-IV | O | 2 | H | endo | 184–185°[1] | 9 |
| 6 | III-IV | O | 2 | H | exo | 166–167°[2] | 9 |
| 7 | III-IV | O | 2 | $CH_3$ | endo | 245–246°[4] | 7 |
| 8 | III-VI | O | 2 | $CH_3$ | endo | 146–147°[2] | 7 |
| 9 | III-VII | O | 2 | $CH_3$ | endo | 210–211°[5] | 7 |
| 10 | III-VIII | O | 2 | $CH_3$ | endo | 216°[6] | 7 |
| 11 | III-V | O | 3 | $CH_3$ | endo | 164–166° | 7 |
| 12 | III-IX | O | 3 | $CH_3$ | endo | 163–164° | 7 |
| 13 | III-X | O | 2 | $CH_3$ | endo |  | 7 |
| 14 | III-XI | O | 2 | $CH_3$ | endo | 91–92° | 7 |
| 15 | III-XII | O | 3 | $CH_3$ | endo |  | 7 |
| 16 | III-XIII | O | 2 | $CH_3$ | endo | 158–159[2] | 7 |
| 17 | III-XIV |  | 2 | $CH_3$ | endo | 159–160[2] | 7 |

D SERIES EXAMPLES

The following compounds of formula I wherein A is a group of formula II or III and D is a group of formula V, are produced:

| Example | A | B | D substit- | M. pt. | Prep. |
|---|---|---|---|---|---|
| 1 | III-I | NH | 3 | 145–147° 154–156°[2] | 7* |
| 2 | III-XII | O | 3 |  | 7 |

*if desired in boiling ethanol

REPRESENTATIVE STARTING MATERIALS OF FORMULA VII

| EXAMPLE | n | $R_8$ | Conf. | B | Characterisation | Trivial name |
|---|---|---|---|---|---|---|
| (a) | 2 | $CH_3$ | endo | O | m. pt. 59–61° | Tropine |
| (b) | 2 | $CH_3$ | exo | O | m. pt. 105–107° | Pseudotropine |
| (c) | 2 | $CH_3$ | endo | NH | bpt 82°/12 mm | Tropinamine |
| (d) | 2 | $CH_3$ | exo | NH | bpt 75°/0.05 mm | Pseudotropinamine |
| (e) | 3 | $CH_3$ | endo | NH | bpt 115°/17 mm |  |
| (f) | 3 | $CH_3$ | endo | OH | amorphous+ |  |
| (g) | 3 | benzyl | endo | OH | m. pt. 69–70°+ |  |
| (h) | 2 | n-$C_3H_7$ | endo | OH | oil++ |  |

+ prepared by reduction of ketone by $NaBH_4$ with separation of isomers
++ prepared by reduction of ketone by $NaBH_4$. Major product.

i) N-methyl-10-aza-bicyclo[4.3.1]dec-8-ylamine 15 g of sodium are reacted in analogous manner to that disclosed below in Example j) with 9.69 g 10-methyl-10-azabicyclo[4.3.1]decan-8-one oxime acetate [m.pt. 253°–253.5° C. prepared in analogous manner to that disclosed in Example A-1b] giving an oil bpt 105°/0.9, mm after working up in conventional manner.

$^1$H.N.M.R. (200 MHz) 3.27–3.04 (multiplet, 2H, HC-(1)- and H-C(6); 2.59 (singlet, 3H, H-C(11)), 2.01–1.49 (multiplet, 13H 6×2H-C and H-C(8)); 1.24 (singlet, 2H; 2.H-N exchangeable with D$_2$O); $^{13}$C N.M.R. (25.2 MHz) 56.41 (d) doublet), 42.85 (quartet C-11), 41.44 (doublet), 37.13 (triplet, C-7 and C-9), 32.54 (triplet, C-2 and C-5) and 24.88 (triplet C-3 and C-4). The configuration is believed to be exo.

j) N-methyl-10-azabicyclo[4.3.1]decan-8-ol 5 g sodium pieces are added to a hot solution of 3.5 g 8-methyl-10-azabicyclo[4.3.1]decan-8-one in 100 ml of dry n-butanol. The mixture is refluxed for an hour, cooled and acidified with concentrated hydrochloric acid to pH 2. The mixture is evaporated to dryness to give a residue which is taken up in sodium hydroxide. The mixture is extracted with chloroform, dried and distilled, b.pt. 90°–95°/0.025 mm.

$^1$H.N.M.R. (200MHz) 4.07–4.23 (multiplet, $^1$H-C-(8)half width ca 20 Hz); 3.63–3.69 (triplet, 0.33 H, j=7 Hz, HO-C-(8) one isomer exchangeable with D$_2$O), 2.13–1.38 (multiplet, 12H, 6×CH$_2$). $^{13}$C.N.M.R. (25.2 MHz) 63.10 (doublet C-8), 56.80 (doublet, C-1 and C-6), 43.13 (quartet, NCH$_3$), 36.30 (triplet-C-7 and C-9), 34.80 (triplet, C-2 and C-5), 25.04 (triplet C-3 and C-4). The configuration is believed to be exo.

In analogous manner to that described in example 2 or 3a there may be made indolyl esters and amides wherein n is 4 and:

| R$_1$ | R$_2$ | R$_3$ | R$_8$ |
|---|---|---|---|
| 6-OH | 2-OEt- | C$_3$H$_7$—CH=CH— | C$_3$H$_7$—CH=CH— |
| 7-NH$_2$ | 2-NH$_2$— | C$_6$H$_5$ | C$_6$H$_5$—(CH$_2$)$_3$ |
| 6-nC$_4$H$_9$—NH— | 2-nC$_4$H$_9$NH— | pMeOC$_6$H$_4$ | pMeO.C$_6$H$_5$(CH$_2$)$_3$ |
| 7-(n-C$_4$H$_9$)$_2$N | 2-(C$_4$H$_9$)$_2$N— | o-FC$_6$H$_4$(CH$_2$)$_3$ | oFC$_6$H$_4$.(CH$_2$)$_3$ |
| 7-SH | 2-SEt- | m-MeC$_6$H$_4$—(CH$_2$)$_3$ | mMeC$_6$H$_4$.(CH$_2$)$_3$ |
| 6-nC$_4$H$_9$S— | 2-n-C$_4$H$_9$S— | m-MeC$_6$H$_4$—(CH$_2$)$_2$ | mMeC$_6$H$_4$.(CH$_2$)$_2$ or CH$_3$ |

Corresponding benzothienyl, benzofuranyl and indenyl compounds with the same R$_1$, R$_2$ and R$_8$ may also be made.

The compounds of the invention exhibit pharmacological activity and are therefore useful as pharmaceuticals, e.g. for therapy.

In particular the compounds exhibit serotonin M receptor antagonist activity as indicated in standard tests. For example, in one test the action of the compounds in inhibiting the action of serotonin in reducing the amplitude of the compound action potential from the isolated rabbit vagus nerve was observed according to the principles of Riccioppo Neto, European Journal of Pharmacology (1978) 49 351–356, under conditions permitting differentiation between action potentials generated in myelinated nerve fibres (A fibres) and those generated in small non-myelinated fibres (C fibres) as described by B. Oakley and R. Schater, Experimental Neurobiology, A Laboratory Manual, University of Michigan Press, 1978, p. 85 to 96. Serotonin itself exerts its effect selectively on the C fibres and reduces the amplitude of the action potential in these fibres progressively with dosage. This action of serotonin is not blocked by the known serotonin antagonists, metitepine, methysergide, BOL-148, which have been said to block D receptors for serotonin, but not M receptors (see Gaddam and Picarelli, Brit. J. Pharmacol. (1957), 12, 323–328). It therefore appears that serotonin reduces the amplitude of the action potential carried by the C fibres through an effect mediated by M receptors for serotonin which are located on these nerve fibres.

The test may be effected by establishing a dose response curve for serotonin ($10^{-7} - 5 \times 10^{-6}$ M) after setting up the nerve. The serotonin is washed out and when the C fibre action potential has regained its original amplitude the compound of the invention at a set concentration of from about $10^{-6}$ M to about $10^{-6}$ M is preincubated with the nerve for 30 to 60 minutes. Varying concentrations of serotonin ($10^{-7}$ to $10^{-4}$ M) are then applied with the compound of the invention at the concentration as was present during the preincubation period.

The M receptor antagonists of the invention either entirely block the action of serotonin (non-competitive antagonist) or cause a parallel shift of the serotonin/dose response curve to the right (i.e. increased concentrations of serotonin were required for effect) (competitive antagonist). The pD′$_2$ of pA$_2$ value may be obtained in the conventional manner.

The serotonin M receptor antagonist activity is also indicated by inhibiting the effect of serotonin on the isolated rabbit heart according to the method of J. R. Fozard and A. T. Moborak Ali, European Journal of Pharmacology, (1978) 49, 109–112 at concentrations of $10^{-11}$ to $10^{-5}$ M of the compound of the invention. pD′$_2$ or pA$_2$ values may be calculated in the conventional manner.

The action of the compounds as serotinin M receptor antagonists for the treatment of analgesia is confirmed by action in the hot plate test at a dose of from about 0.01 to 100 mg/kg s.c. or p.o.

The serotonin M receptor antagonist activity is furthermore indicated in the cantharidine blister base test at a concentration of about $10^{-8}$ M. A blister is produced on the skin of the forearm of human volunteers with cantharidine. When serotonin is applied to the base of such blisters it produces pain which can be measured, the intensity being proportional to the concentration of serotonin applied. The procedure has been described by C. A. Keele and D. Armstrong in Substances producing Pain and Itch, Edward Arnold, London, 1964, p. 30 to 57. This algesic action of serotonin is not inhibited by the serotonin D receptor-antagonists such as lysergic acid diethylamide or its bromo derivative and is therefore believed to be mediated by M receptors.

In the procedure followed the area under the curve instead of the peak amplitude is measured by a linear integrator coupled to a pain intensity indicator which is operated by the volunteer. With increasing concentrations of serotonin a cumulative dose-response curve to serotonin may be obtained. When no further response on increasing the serotonin concentration is obtained, the serotonin is washed off and the blister incubated with physiological buffer solution for at least 40 minutes before the compound of the invention, is applied. The test substance is preincubated with the blister base for 30 minutes at a concentration of about $10^{-8}$ M before varying concentrations of serotonin are applied. A $pA_2$ value may be obtained in the conventional manner.

The compounds of the invention are therefore useful as serotonin M receptor antagonists, e.g. for the treatment of pain, especially migraine, vascular and cluster headaches and trigeminal neuralgia and also for the treatment of heart circulation disorders, e.g. for the treatment of sudden death, and possibly as antipsychotics.

For this use the dosage will, of course, vary depending on the compound employed, mode of administration and treatment desired. However, in general, satisfactory results are obtained when administered at a daily dosage of from about 0.1 mg to about 40 mg per kg animal body weight, conveniently given in divided doses 2 to 4 times a day or in sustained release form. For the larger mammals, the total daily dosage is in the range from about 0.5 to about 500 mg, and dosage forms suitable for oral administration comprise from about 0.2 mg to about 250 mg of the compounds admixed with a solid or liquid pharmaceutical carrier or diluent.

The compounds of the invention furthermore exhibit anti-arrhythmic activity as indicated by their serotonin M receptor antagonist activity and in standard tests. For example the compounds inhibit arrhythmias induced by norepinephrine in anaesthetized rats. In this test infusions of norepinephrine (3 to 10 microgram/animal body weight) are given until an arrhythmic phase as indicated by ECG measurements lasts longer than 10 seconds duration. After control of 3 consecutive injections of norephinephrine the compound of the invention is injected at from about 10 to about 500 microgram/kg animal body weight followed by norepinephrine injections. The arrhythmic phase is reduced, or abolished depending on the dose of test compound.

The compounds are useful as anti-arrhythmic agents. For this use the dosage will, of course, vary depending on the compound employed, mode of administration and treatment desired. However, in general, satisfactory results are obtained when administered at a daily dosage of from about 10 micrograms to about 10 milligrams per kg animal body weight, conveniently given in divided doses 2 to 4 times a day or in sustained release form. For the larger mammals, the total daily dosage is in the range from about 0.05 to about 500 mg, and dosage forms suitable for oral or conveniently intravenously administration comprise from about 0.2 mg to about 250 mg of the compounds admixed with a solid or liquid pharmaceutical carrier or diluent.

The present invention accordingly provides a compound of the invention in pharmaceutically acceptable form, e.g. in free base form, or pharmaceutically acceptable acid addition salt form or quaternary ammonium salt form, for use as a pharmaceutical, particularly for use as a serotonin M antagonist for those diseases where blockage of serotonin M receptors would be expected to have benficial effects, e.g. as an analgesic agent, especially as an anti-migraine agent and as an anti-arrhythmic agent.

The preferred indication is the analgesic indication.

The compounds of the invention may be administered in free base form, or in pharmaceutically acceptable salt form, e.g. suitable acid addition salts and quaternary ammonium salts. Such salts exhibit the same order of activity as the free bases. The present invention accordingly also provides a pharmaceutical composition comprising a compound of the invention, in particular a compound of formula I, an acid addition salt thereof or a quaternary ammonium salt thereof, in association with a pharmaceutical carrier or diluent. Such compositions may be formulated in conventional manner so as to be for example a solution or a tablet.

The compounds of the invention may be administered in analogous manner to that used for clinically used drugs for the utility conceived, for example metoclopramide in the case of migraine (see J. B. Hughes Medical Journal of Australia (1977), p. 580, (issue of Oct. 22, 1977)) where an intravenous injection of 10 mg metoclopramide was satisfactory. The exact dose for a particular compound will depend on a number of factors, in particular the relative potency. It has been determined that a representative compound of the present invention, the compound of Example C-2, has a $pA_2$ value of 11 in the above rabbit heart test compared with a $pA_2$ value for metoclopramide of 7.1. It is therefore indicated that these compounds may be administered at the same or lower doses than metoclopramide.

A group of compounds comprises compounds of formula I wherein A is a group of formula II, wherein $R_1$ and $R_2$ independently are hydrogen, halogen ($C_{1-4}$)alkyl, or ($C_{1-4}$)alkoxy, $R_1$ is in the 4 or 5 positions, $R_3$ is hydrogen or ($C_{1-4}$)alkyl, the free valence is in position 4 or 5; a group of formula III wherein $R_4$ is hydrogen, halogen or ($C_{1-4}$)alkoxy, $R_5$ is hydrogen or halogen, $R_6$ is amino, nitro, ($C_{1-4}$)alkylamino, di-($C_{1-4}$)alkylamino or halogen, or 1-pyrrolyl, $R_7$ is hydrogen or halogen, D is a group of formula IV wherein $R_8$ is hydrogen, ($C_{1-4}$)alkyl or benzyl or a group of formula V wherein the free valence is attached to the 3 position and subject to the above proviso to formula I.

A group of compounds comprises the compounds of the above formula I excluding any one of the specific examples.

In a 1st group of compounds X is —$CH_2$—.
In a 2nd group of compounds X is —$NR_3$—.
In a 3rd group of compounds X is —O—.
In a 4th group of compounds X is —S—.
In a 5th group $R_1$ is H.
In a 6th group $R_1$ is alkyl.
In a 7th group $R_1$ is halogen.
In a 8th group $R_1$ is alkoxy.
In a 9th group $R_2$ is hydrogen.
In a 10th group $R_2$ is alkyl.
In a 11th group $R_2$ is halogen.
In a 12th group $R_2$ is alkoxy.
In a 13th group $R_3$ is hydrogen.
In a 14th group $R_3$ is alkyl.
In a 15th group $R_3$ is aralkyl.
In a 16th group $R_4$ is halogen.
In a 17th group $R_4$ is alkylamino.
In a 18th group $R_4$ is alkoxy.
In a 19th group $R_5$ is amino.
In a 18th group $R_5$ is alkylamino.
In a 19th group $R_5$ is dialkylamino.
In a 20th group $R_6$ is hydrogen.
In a 21st group $R_6$ is halogen.
In a 22nd group B is 0.
In a 23rd group B is NH.

In a 24th group n is 2.
In a 25th group n is 3.
In a 26th group n is 4.
In a 27th group $R_8$ is H.
In a 28th group $R_8$ is alkyl.
In a 29th group $R_8$ is aralkyl.
In a 30th group D is a group of formula V.

We claim:

1. A method of inducing a serotonin M receptor antagonist effect comprising administering to a subject in need of such treatment a therapeutically effective amount of a compound of formula Isb:

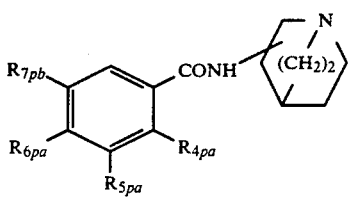

wherein
- $R_{4pa}$ is halogen, $(C_{1-4})$alkylamino or $(C_{1-4})$alkoxy;
- $R_{5pa}$ is hydrogen;
- $R_{6pa}$ is amino, $(C_{1O4})$alkylamino or di$(C_{1-4})$alkylamino; and
- $R_{7pb}$ is hydrogen or halogen;

or a pharmaceutically acceptable acid addition or quaternary ammonium salt thereof.

2. A method according to claim 1 comprising administering a therapeutically effective amount of a compound having the formula

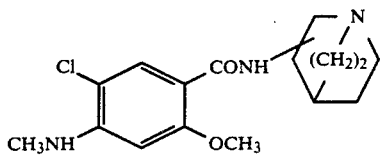

or a pharmaceutically acceptable acid addition or quaternary ammonium salt thereof.

* * * * *